United States Patent
Shapiro

(10) Patent No.: US 7,297,834 B1
(45) Date of Patent: Nov. 20, 2007

(54) SURGICAL SPONGE IDENTIFICATION SYSTEM AND METHOD

(76) Inventor: Michael Evan Shapiro, 621 14th Green, Incline Village, NV (US) 89509

(*) Notice: Subject to any disclaimer, the term of this patent is extended or adjusted under 35 U.S.C. 154(b) by 0 days.

(21) Appl. No.: 11/014,191

(22) Filed: Dec. 15, 2004

Related U.S. Application Data

(63) Continuation-in-part of application No. 10/861,919, filed on Jun. 4, 2004.

(60) Provisional application No. 60/539,384, filed on Jan. 26, 2004.

(51) Int. Cl.
*A61F 13/20* (2006.01)

(52) U.S. Cl. .................. 604/362; 604/365; 604/367; 604/356; 604/374

(58) Field of Classification Search ................ 604/362, 604/361, 363, 364, 365, 367, 356, 374
See application file for complete search history.

(56) References Cited

U.S. PATENT DOCUMENTS

| | | | | |
|---|---|---|---|---|
| 3,097,649 | A | | 7/1963 | Gray ........................ 128/296 |
| 3,468,694 | A | * | 9/1969 | Werner et al. ............... 427/280 |
| 3,941,132 | A | * | 3/1976 | Lenaghan ................... 604/377 |
| 3,963,428 | A | * | 6/1976 | Stark ............................. 8/485 |
| 3,977,406 | A | * | 8/1976 | Roth ......................... 604/362 |
| 4,114,601 | A | | 9/1978 | Abels ........................ 128/1 R |
| 4,193,405 | A | | 3/1980 | Abels ........................ 128/296 |
| 4,244,369 | A | * | 1/1981 | McAvinn et al. ........... 604/362 |
| 4,658,818 | A | | 4/1987 | Miller, Jr. et al. ........ 128/303.1 |
| 4,832,198 | A | * | 5/1989 | Alikhan ..................... 206/438 |
| 4,917,694 | A | * | 4/1990 | Jessup ........................ 604/362 |
| 5,045,080 | A | * | 9/1991 | Dyer et al. ................. 604/362 |
| 5,057,095 | A | | 10/1991 | Fabian ....................... 604/362 |
| 5,105,829 | A | | 4/1992 | Fabian et al. ............... 128/899 |
| 5,107,862 | A | | 4/1992 | Fabian et al. ............... 128/899 |
| 5,188,126 | A | | 2/1993 | Fabian et al. ............... 128/899 |
| 5,190,059 | A | | 3/1993 | Fabian et al. ............... 128/899 |
| 5,302,392 | A | * | 4/1994 | Karakelle et al. ........... 424/409 |
| 5,329,944 | A | | 7/1994 | Fabian et al. ............... 128/899 |
| 5,456,718 | A | | 10/1995 | Szymaitis ..................... 623/11 |
| 5,629,498 | A | | 5/1997 | Pollock et al. ................ 177/15 |
| 5,650,596 | A | | 7/1997 | Morris et al. ............. 177/25.13 |
| 5,897,797 | A | * | 4/1999 | Drouillard et al. ...... 219/121.68 |
| 5,923,001 | A | | 7/1999 | Morris et al. ............. 177/245 |
| 5,931,824 | A | * | 8/1999 | Stewart et al. ............. 604/358 |
| 6,013,347 | A | * | 1/2000 | Martin et al. ................. 428/92 |
| 6,026,818 | A | | 2/2000 | Blair et al. ................. 128/899 |
| 6,366,206 | B1 | | 4/2002 | Ishikawa et al. ......... 340/573.1 |
| 2002/0032435 | A1 | | 3/2002 | Levin ............................ 606/1 |
| 2002/0143320 | A1 | | 10/2002 | Levin ............................ 606/1 |
| 2003/0006762 | A1 | | 1/2003 | Clements .................... 324/239 |
| 2005/0203470 | A1 | * | 9/2005 | Ballard ....................... 604/362 |

OTHER PUBLICATIONS

Results of STIC search: Recommended Practices for Sponges, Sharp and Instrument Counts, Abstr., 13 pp. total.*

* cited by examiner

*Primary Examiner*—Tatyana Zalukaeva
*Assistant Examiner*—Ginger T. Chapman
(74) *Attorney, Agent, or Firm*—Sierra Patent Group, Ltd.

(57) ABSTRACT

A surgical sponge identification system for a set of surgical sponges comprising each sponge in the set having an exterior surface, each sponge bearing on the exterior surface a unique indicium from a set of indicia uniquely identifying the set.

3 Claims, 1 Drawing Sheet

SURGICAL SPONGE IDENTIFICATION SYSTEM AND METHOD

CROSS-REFERENCE TO RELATED APPLICATIONS

This application is a continuation-in-part of patent application Ser. No. 10/861,919, filed Jun. 4, 2004, which claims priority to U.S. Provisional Application Ser. No. 60/539,384, filed Jan. 26, 2004, both of which are hereby incorporated by reference as if set forth herein.

BACKGROUND

The present invention relates to Surgical Sponge designs and means for identifying surgical sponges.

Error in the practice of medicine is common and may cause harm to patients. One persistent and poorly understood error is leaving surgical sponges or instruments inside patients who undergo surgery. Incidents of leaving surgical sponges in the patient may result in injury and even death. Some studies suggest that errors of this nature occur in 1 of every 1000 intra-abdominal operations. Understanding why these errors occur leads to various measures of prevention.

Standards exist that have long required that only sponges detectable via radiography be used. The standard requires that sponges are to be counted once at the start and twice at the end of all surgical procedures. If not all sponges are accounted for, radiography and/or a manual re-exploration is performed. Despite the procedural safeguards, foreign bodies go undetected and are left in the patient.

The prior art methods of detection of the foreign objects include the use of radiography. Radiography is employed when counts of surgical sponges are deemed to indicate a miscount or deemed in error. The radiographic screening is ideally performed prior to the patient leaving the operating room. However, the current use of radiography varies widely. Often due to the lack of readily available radiographic equipment and the urgency to process the patient out of the operating room, radiography is not a consistent and thorough means of detection.

The result of inadequate procedures and devices to detect the inadvertently left behind foreign bodies can give rise to expensive malpractice claims expenses alone.

What is needed in the art is a reliable and simplified device and method of tracking surgical sponges in patients.

SUMMARY

According to one aspect of the present invention, a surgical sponge and a surgical sponge identification system comprise at least one set of sponges associated with a set of identifier labels, each sponge bearing one identifier label from the set of identifier labels. The identifier label is disposed on the outer surface of the sponge and can comprise, for example, a surgical suture or other sterile thread woven or stitched into the sponge or an identifier printed onto the sponge with sterile ink. The label comprises one of characters and signs uniquely identifying the body from any other surgical sponge body. Application of the identification label may be achieved by any method compatible with human tissue, including, but not limited to, the use of sterile threads and sterile inks as mentioned above, stamping mechanisms, compression mechanisms, and sowing mechanisms.

A method according to the present invention comprises using at least one set of sponges during a surgical procedure. As each sponge is removed its identifier is tallied against the identifiers for the entire set of sponges. Once the tally accounts for all sponges in the set, it is known that all sponges in the set have been removed. The same procedure is followed for each set of sponges used during the procedure.

DETAILED DESCRIPTION

A surgical sponge identification system is disclosed. The surgical sponge identification system comprises an identification label disposed on each surgical sponge and visible to a health care provider. The identification can be numerals or letters. Application of the identification label may be achieved by any method compatible with human tissue, including, but not limited to, the use of sterile threads, sterile inks, stamping mechanisms, compression mechanisms, and sowing mechanisms. The identification label can comprise, for example, biodegradable FDA approved surgical suture material. The suture material can be woven into the structure of the surgical sponge. A set of surgical sponges having a set of identification labels may be provided in packages. The packages may be identified by information associating it with the set of identification labels.

Figure 1:
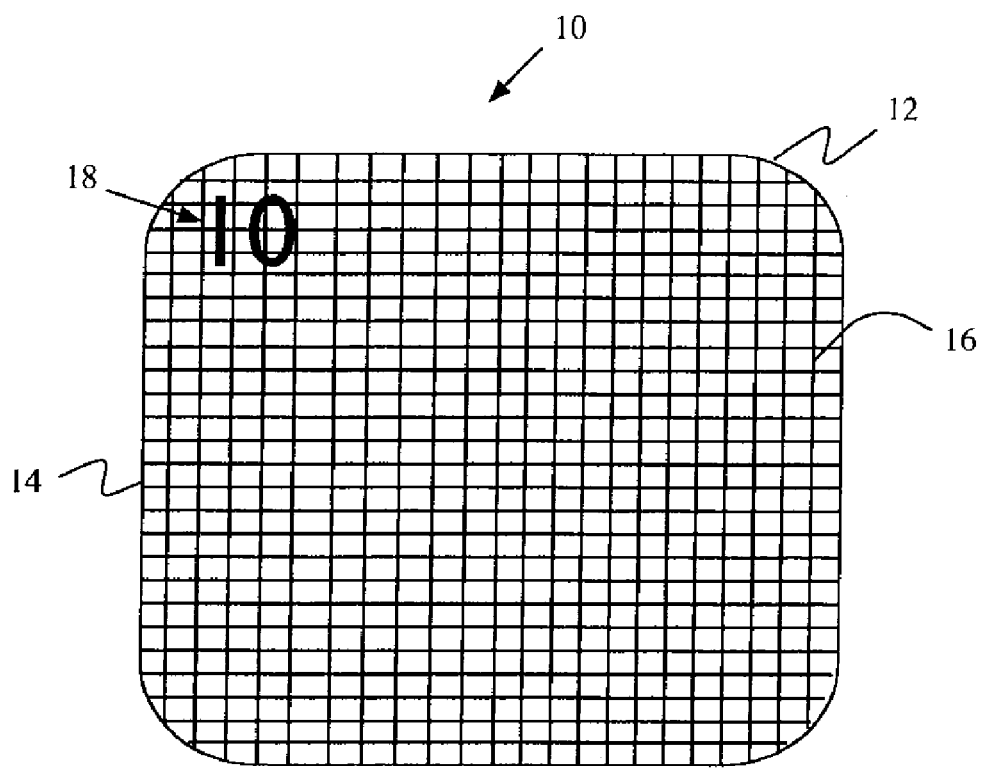
FIG. 1 is a plan view of an exemplary surgical sponge with an identifier label.
Figure 2:
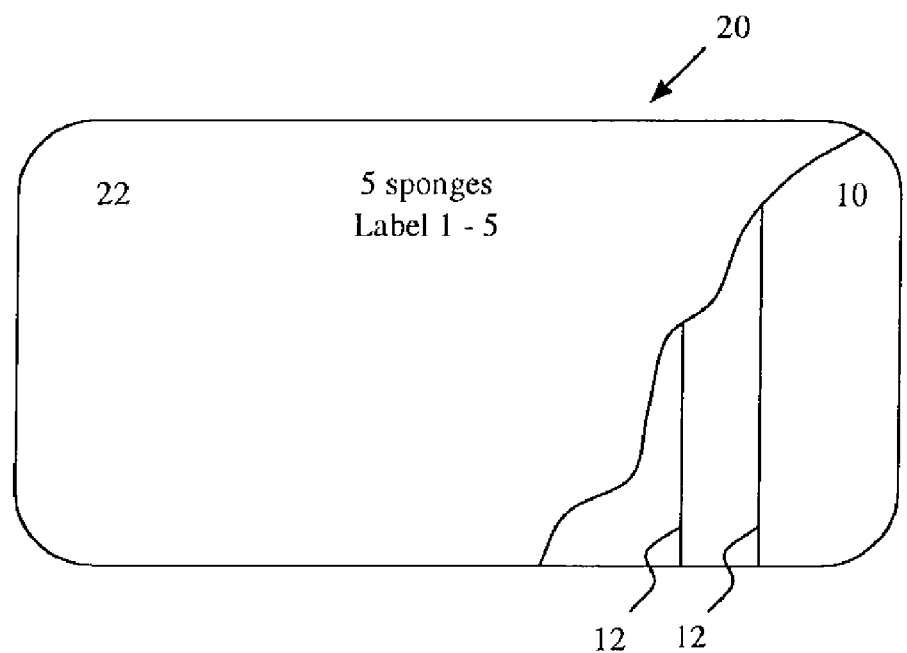
FIG. 2 is a partial cutaway plan view of an exemplary surgical sponge package.

Referring to FIGS. 1 and 2, an exemplary surgical sponge identification system is illustrated. The surgical sponge 12 comprises a body 14 formed in a structure of fibers that interlock to form a pad of material 16. The sponge 12 can be configured in a rectilinear or other shape. A label 18 is formed on the outer surface of the body 14. The label may comprise a surgical suture woven into the pad of material 16 or a sterile ink printed onto the pad. The label 18 can withstand the wear and tugging of surgical instruments during use. Label 18 comprises or bears a unique identification number in order to provide a means to distinguish each individual surgical sponge 12. Label 18 can be read even in fluid or air medium (e.g., human blood). Label 18 can be sterilized for one time use. The label 18 can be colored an off white color so as to be more visible during use when the surgical sponge 12 is soaked with body fluids. The material composition of the label 18 poses no additional risks to patients since the material can be a biodegradable FDA approved surgical suture or other approved material.

In an exemplary embodiment, the label 18 can comprise Arabic numerals in a consecutive order (e.g., 1 through 10). The label 18 can also comprise alphabetical symbols (e.g. A, B, C, D, E). It is contemplated that any alphabet, or system of characters or signs can be employed in the label 18. Each surgical sponge 12 has a unique identifier in the label 18.

A quantity of surgical sponges 12 can be assembled into a package 20. The package 20 has a package label 22. The package label 22 includes an indication of the quantity of surgical sponges 12 contained as well as a listing of the labels 18 used to individually identify each individual surgical sponge 12 contained in the package 20. In an exemplary embodiment, the package 20 contains a quantity of five surgical sponges 12, the surgical sponges 12 have labels 18 bearing numbers from "1" through "5".

According to one aspect of the present invention, the surgical sponge identification system 10 can include many packages 20 that have a consecutive order of numerical identifiers on each set of five sponges 12 contained therein. In an exemplary embodiment, another package 20 can contain five surgical sponges 12 having labels 18, 6 through 10 and another package 20 can contain five surgical sponges 12 having labels 18 indicating 11-15. The pattern of labeling can be repeated at length.

In use, the surgical sponge identification system 10 can be used to track each and every single surgical sponge 12 used. At the beginning of a surgical case, a health care provider can take a first package 20 containing surgical sponges labeled, for example, with consecutive numbers from "1" through "5". After having dispensed these sponges and having used them in the procedure, the health care provider can take a second package 20 containing surgical sponges labeled, for example, f with consecutive numbers from "6" through "10". The health care provider documents the dispensing of the surgical sponges and also performs a count and a recount of the sponges used.

As the surgical sponges 12 are removed from the patient, the health care provider places the sponges back into the containers from which they came. The sponges numbered 1 through 5 are placed back into the first package 20. The surgical sponges labeled 6 through 10 are placed back into the second container 20. The health care provider verifies the containers with the associated surgical sponges. At the end of the case, the surgical sponges used are checked to ensure that the containers that have been opened and each surgical sponge that has been dispensed is properly contained and accounted.

A miscount or a sponge that has not been located in the proper container can trigger a recount and a search. The patient will be searched for the surgical sponges that are not properly accounted. The search and recount can be performed until all surgical sponges are properly accounted. One advantage of using the method of the present invention is that the number of the missing sponge can often provide a clue as to where it may be found. For example, if sponge number "3" is missing after performing a two-hour surgical procedure, the surgeon knows that it was probably used during the first part of the surgery. This information may provide a suggestion of where to look for the missing sponge.

The surgical sponge identification system can be consistently applied. The surgical sponge identification system can allow a surgical team to reliably and safely maintain a surgical sponge inventory and count during cases. The surgical sponge identification system allows for a cost effective method to increase reliability. The surgical sponge identification system can prevent the unnecessary loss of surgical sponges and the subsequent pain and suffering of patients. The surgical sponge identification system can reduce the costs of medical malpractice insurance. The surgical sponge identification system can prevent unnecessary additional surgery to remove the lost surgical sponges and the increased risk associated with the additional surgery.

While embodiments and applications of this disclosure have been shown and described, it would be apparent to those skilled in the art that many more modifications than mentioned above are possible without departing from the inventive concepts herein. The disclosure, therefore, is not to be restricted except in the spirit of the appended claims.

What is claimed is:

1. A method for accounting for missing surgical sponges used in a patient during a surgical procedure, comprising:
   providing a set of surgical sponges, each sponge in said set comprising a body formed in a structure of fibers that interlock to form a pad of material having an exterior surface, said exterior surface bearing a unique indicium from a set of indicia uniquely identifying said set, wherein each sponge in said set is disconnected from the other sponges in said set, wherein said unique indicium comprises sterile ink that has been applied to said exterior surface using a stamping mechanism, and wherein said indicia comprises a set of consecutive numbers;
   using individual sponges from said set in the surgical procedure in an order related to their individual indicium;
   collecting said sponges as they are removed from the patient;
   tallying said indicium of each collected sponge against the set of indicia for the set of sponges; and
   searching the patient to locate missing sponges, wherein the unique indicia correlate with timing of the surgical procedure, thereby suggesting to a surgeon where to look for a missing sponge.

2. The method of claim 1, wherein collecting said sponges as they are removed from the patient includes placing each of said sponges in a container associated with said set.

3. The method of claim 1, further including:
   providing a second set of surgical sponges, each sponge in said second set comprising a body formed in a structure of fibers that interlock to form a pad of material having an exterior surface, said exterior surface bearing a unique indicium from a set of indicia uniquely identifying said second set, wherein said unique indicium comprises sterile ink that has been applied to said exterior surface using a stamping mechanism, and wherein said indicia comprises a set of consecutive numbers;
   using individual sponges from said second set in the surgical procedure in an order related to their individual indicium;
   collecting said sponges from said second set as they are removed from the patient; and
   tallying said indicium of each collected sponge against the set of indicia for said second set of sponges.

* * * * *